United States Patent
Osypka et al.

(10) Patent No.: US 7,186,219 B2
(45) Date of Patent: Mar. 6, 2007

(54) CALIBRATION OF A DOPPLER VELOCIMETER FOR STROKE VOLUME DETERMINATION

(75) Inventors: Markus J. Osypka, Knuellwald (DE); Donald P. Bernstein, Rancho Santa Fe, CA (US)

(73) Assignee: Osypka Medical GmbH, Berlin (DE)

( * ) Notice: Subject to any disclaimer, the term of this patent is extended or adjusted under 35 U.S.C. 154(b) by 313 days.

(21) Appl. No.: 10/268,120

(22) Filed: Oct. 10, 2002

(65) Prior Publication Data
US 2003/0163056 A1    Aug. 28, 2003

Related U.S. Application Data

(60) Provisional application No. 60/328,630, filed on Oct. 11, 2001.

(51) Int. Cl.
A61B 5/02     (2006.01)
A61B 5/04     (2006.01)
A61B 5/08     (2006.01)

(52) U.S. Cl. .................. 600/504; 600/505; 600/526; 600/468

(58) Field of Classification Search ............... 600/505, 600/547, 478–480, 465
See application file for complete search history.

(56) References Cited

U.S. PATENT DOCUMENTS

| | | | |
|---|---|---|---|
| 3,340,867 A | 9/1967 | Kubicek et al. | |
| 4,450,527 A | 5/1984 | Sramek | |
| 4,509,526 A * | 4/1985 | Barnes et al. ............... | 600/456 |
| 4,562,843 A | 1/1986 | Djordjevich et al. | |
| 4,807,638 A | 2/1989 | Sramek | |
| 4,836,214 A | 6/1989 | Sramek | |
| 4,858,614 A | 8/1989 | Stevens et al. | |
| 4,953,556 A | 9/1990 | Evans | |
| 5,052,395 A | 10/1991 | Burton et al. | |

(Continued)

FOREIGN PATENT DOCUMENTS

EP    1 247 487    10/2002

(Continued)

OTHER PUBLICATIONS

Wallace, Arthur W.; "Endotracheal Cardiao Output Monitor"; Anesthesiology; vol. 92: 178-89; Jan. 2000.

*Primary Examiner*—Robert L. Nasser
(74) *Attorney, Agent, or Firm*—Martin & Ferraro, LLP

(57) ABSTRACT

Doppler Velocimetry is a widely used method for estimating stroke volume (SV). The accuracy and reliability of its measurement however, is dependant on
a) the correct assessment of the aortic valve cross-sectional area (CSA), and
b) the maximal systolic velocity integral (SVI).
The invention avoids the conventional assessment of aortic valve CSA by using a calibration method: a reference stroke volume $SV_{REF}$ is determined by a method different from Doppler velocimetry, e.g. by thoracic electrical bioimpedance (TEB), or thoracic electrical bioadmittance, measured via surface thorax electrodes (transthoracic approach) or via electrodes located directly on an esophageal catheter/probe (esophageal approach). In the latter case, if esophageal Doppler velocimetry is used, the same catheter can be used for the placement of the electrodes and for an ultrasound transducer. In the case of esophageal Doppler velocimetry, an additional benefit of the invention is that the Doppler catheter/probe does not need to be aimed precisely at the site of maximum flow amplitude, as long as a stable catheter/probe location is maintained within the esophagus.

19 Claims, 2 Drawing Sheets

U.S. PATENT DOCUMENTS

| | | |
|---|---|---|
| 5,103,828 A | 4/1992 | Sramek |
| 5,178,154 A | 1/1993 | Ackmann et al. |
| 5,188,106 A * | 2/1993 | Nappholz et al. ............. 607/24 |
| 5,309,917 A | 5/1994 | Wang et al. |
| 5,316,004 A | 5/1994 | Chesney et al. |
| 5,423,326 A | 6/1995 | Wang et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,685,316 A | 11/1997 | Schookin et al. |
| 5,782,774 A | 7/1998 | Shmulewitz |
| 5,791,349 A | 8/1998 | Shmulewitz |
| 6,016,445 A | 1/2000 | Baura |
| 6,058,325 A | 5/2000 | Baura |
| 6,095,987 A | 8/2000 | Shmulewitz et al. |
| 6,102,869 A | 8/2000 | Meier et al. |
| 6,161,038 A | 12/2000 | Schookin et al. |
| 6,169,914 B1 * | 1/2001 | Hovland et al. ............ 600/340 |
| 6,186,955 B1 | 2/2001 | Baura |
| 6,490,474 B1 * | 12/2002 | Willis et al. ................ 600/424 |

FOREIGN PATENT DOCUMENTS

| | | |
|---|---|---|
| WO | WO 89/04634 | 6/1989 |

* cited by examiner

CALIBRATION OF A DOPPLER VELOCIMETER FOR STROKE VOLUME DETERMINATION

This application claims the benefit of U.S. provisional application No. 60/328,630, filed Oct. 11, 2001, of which is incorporated herein by reference.

BACKGROUND OF THE INVENTION

1. Field of the Invention

The present invention relates to a method and an apparatus for monitoring the stroke volume and the cardiac output of a subject's heart at different times, in particular during the course of a surgical operation.

2. Description of the Related Art

During the course of a surgical operation of a (human) subject, it is of paramount importance to monitor the function of the subject's heart. One important piece of information the surgeon is interested in is the left ventricular stroke volume (SV) of that heart. Furthermore, the surgeon might be interested in the cardiac output (CO), which is equivalent to the stroke volume multiplied by the heart rate (HR).

A well-known and reliable method of determining the stroke volume is by thoracic electrical bioimpedance or bioadmittance analysis. The transthoracic electrical bio-impedance/bioadmittance measurement method has been proposed by Kubicek and Sramek (U.S. Pat. Nos. 3,340,867 and 4,450,527, which are incorporated herein by reference). Esophageal electrical bioimpedance/bioadmittance measurements are, for example, known from U.S. Pat. No. 4,836,214 to Sramek, which is also incorporated herein by reference.

When the thorax of the patient is opened during a surgical operation, thoracic electrical bioimpedance or bioadmittance measurements are no longer meaningful. Therefore, in these cases, usually ultrasonic Doppler velocimetry is used for the determination of the left ventricular stroke volume SV and the cardiac output CO. In the related art, mostly the ascending thoracic aorta is interrogated when the patient is under anesthesia. The principle underlying the ultrasonic measurement of SV is quite simple:

If the distance (d, measured in cm) traversed by a cylindrical column of blood is measured over its ejection interval (t, measured in s) and multiplied by the measured cross-sectional area conduit (CSA, measured in $cm^2$) through which it flows, then SV (measured in ml) can be calculated as:

$$SV = CSA \cdot d.$$

The CSA of the aorta is calculated via diameter measurements employing ultrasonic echo imaging. The distance d is calculated using facsimiles of blood velocity extracted from ultrasonic Doppler velocimetry.

According to the Doppler principle, when an emitted ultrasonic wave of constant magnitude is reflected (backscattered) from a moving object (red blood cell), the frequency of the reflected ultrasound is altered. The difference in frequency between the ultrasound emitted ($f_0$) and that received ($f_R$) by the Doppler transducer produces a frequency shift $\Delta f = f_R - f_0$. This instantaneous frequency shift depends upon the magnitude of the instantaneous velocity of the reflecting targets, their direction with respect to the Doppler transducer, and the cosine of the angle at which the emitted ultrasound intersects these targets. The instantaneous Doppler frequency shift $\Delta f_T$ is thus, like velocity, a vector, since it possesses the characteristics of both magnitude and direction. Instantaneous red blood cell velocity, $v_i$, are related by the Doppler equation, which was derived by W. R. Milnor ("Methods of measurement", in: Hemodynamics. Milnor W R (ed). Baltimore, Williams & Wilkins Co, 1982, p. 272, incorporated herein by reference), and is given as:

$$\Delta f_T = \frac{2 \cdot f_0 \cdot \cos\theta}{C} \cdot v_i$$

where $\Delta f_T$ is the instantaneous frequency shift; $f_0$ the emitted constant magnitude ultrasonic frequency; C is the speed (propagation velocity) of ultrasound in tissue (blood) (1540–1570 m/s); $\theta$ is the incident angle formed by the axial flow of red blood cells and the emitted ultrasonic signal; and $v_i$ is instantaneous velocity of red cells within the scope of the interrogating ultrasonic perimeter or target volume.

By algebraic rearrangement:

$$v_i = \frac{C}{2 \cdot f_0} \cdot \frac{\Delta f_T}{\cos\theta}.$$

Since C and $f_0$ are constants, then:

$$v_i = k \cdot \frac{\Delta f_T}{\cos\theta}.$$

If the angle of incidence between the axial flow of blood and the ultrasonic beam is 0°, i.e. $\theta = 0°$, then cosine $\theta$ equals 1, and thus:

$$v_i = k \cdot \Delta f_T$$

$$v_i \approx \Delta f_T$$

Since from the opening of the aortic valve, velocity rapidly accelerates from 0 to reach a maximum (peak velocity) during the first ⅓ or ½ of the ejection phase of systole and a more gradual deceleration phase back to 0 velocity ensues with the closure of a competent aortic valve, $V_i$ is not a constant. Therefore, in order to obtain the distance d traversed by the cylindrical column of blood according to the model described above, $V_i$ has to be integrated over time, from the point in time $t_0$ representing the opening of the aortic valve to $t_1$ representing the closure of the aortic valve. Thus, $$d(t) = \int_{t_0}^{t_1} v_i(t) dt = SVI$$

where this integral is called the systolic velocity integral SVI and defines the stroke distance in centimeters.

The systolic velocity integral (SVI) may be found by planimetry using a microcomputer (see Goldberg S J, Allen H D, Marx G R, et al., "Flow computation", in: Doppler echocardiography. Goldberg S J, Allen H D, Marx G R, et al (eds), Philadelphia, Lea & Febiger, 1985, p. 68, incorporated herein by reference), or by simple triangulation (see Haites N E, McLennan F M, Mowat D H R, et al., "Assessment of cardiac output by the Doppler ultrasound technique alone", Br Heart J 1985, vol. 53, p. 123, incorporated herein by reference). Since the waveform closely describes a triangle, the formula $$\frac{b \cdot h}{2}$$

may sometimes be legitimately employed (see Main J, Nanda N. C, Saini V D, "Clinically useful Doppler calculations and illustrative case examples", in: Doppler echocardiography. Nanda N C (ed). N. Y. Igaku-Shoin, 1095, p. 488, incorported herein by reference); b refers to $T_{LVE}$ and h represents peak velocity ($v_{MAX}$). Although substantial error may occur with this oversimplification (see Distante A, Moscarelli E, Rovai D, et al., "Monitoring of changes in cardiac output by transcutaneous aortovelocigraphy, a noninvasive Doppler technique: Comparison with thermodilution", in J Nucl Med All Sci 1980, vol. 24, p. 171, incorporated herein by reference), Haites et al. (cited and incorporated above) reported good correlation (r=0.98) with little variability between triangulation and planimetry. Gardin et al. (see Gardin J M, Tobis J M, Dabestani A, et al., "Superiority of two-dimensional measurements of aortic vessel diameter in Doppler echocardiographic estimates of left ventricular stroke volume", in: J Am Coll Cardiol 1985, vol. 6, p. 66, incorporated herein by reference) have proposed an equation that more closely approximates the planimetered area:

$$SVI_{PLANIMETRY} = 1.14 \cdot (0.5 \cdot v_{MAX} \cdot T_{LVE}) + 0.3 \text{ cm,}$$

where $v_{MAX}$ is the peak ejection velocity and $T_{LVE}$ equals the left ventricular ejection time ($T_{LVE}$).

As mentioned above, in Doppler velocity measurements of SV, it is assumed that the volume of blood ejected over a single ejection interval possesses the geometric proportions of a circular cylinder. Hence, the systolic velocity integral has to be multiplied with the cross-section area of a circle having a radius r, $$SV = \pi r^2 \cdot SVI.$$

If the mean diameter $\overline{D}=2\overline{r}$ of a finite segment of the ascending aorta is measured and an SVI is defined at the point of that measurement, the stroke volume SV is calculated as $$SV = \pi \left(\frac{\overline{D}}{2}\right)^2 \cdot \int_{t_0}^{t_1} v_i(t) dt = \overline{CSA} \cdot SVI.$$

The measurement of the mean diameter and thus the mean cross-section area of the ascending aorta is performed by ultrasonic echo-imaging. SVI is measured by either continuous-wave or pulse-mode Doppler velocimetry.

In view of the large number of assumptions made when developing the latter equation, it is clear that the prior art Doppler velocimetry is not as exact as many other methods of determining stroke volume (SV) and cardiac output (CO), see Gardin et al. cited above (Donovan K D, Dobb G J, Newman M A, et al., "Comparison of pulsed Doppler and thermodilution methods for measuring cardiac output in critically ill patients", in: Crit Care Med 1987, vol. 15, p. 853; Waters J, Kwan O L, Kerns G, et al., "Limitations of Doppler echocardiography in the calculation of cardiac output", in: Circulation 1982, vol. 66 (Supp II), p. 122; Waters J, Kwan O L, DeMaria A N, "Sources of error in the measurement of cardiac output by Doppler techniques", in: Circulation 1983, vol. 68 (Suppl III), p. 229, all of which are incorporated herein by reference). A first assumption that is not really valid is that the blood flows in the ascending aorta in an undisturbed laminar flow. Under some conditions, however, the flow can be turbulent.

Another important problem is that the assumption of a circular aorta of constant internal diameter is only fulfilled superficially in a largely undetermined patient population. In fact, aortas of many patients are oval or have the shape of an irregular circle. Furthermore, the ascending aorta is also not rigid, as assumed, since it pulsates during systolic ejection producing 5% to 17% changes in the cross-sectional area from its diastolic to systolic pressure extremes (see Greenfield J C, Patel D J, "Relation between pressure and diameter in the ascending aorta of man", in: Circ Res 1962, vol. 10, p. 778, which is incorporated herein by reference). Moreover, even if the aorta was circular, the measurement accuracy of any echocardiographic method is limited by the resolution of existing commercial equipment. Mark et al. (see Mark J B, Steinbrook R A, Gugino L D, et al., "Continuous noninvasive monitoring of cardiac output with esophageal Doppler ultrasound during cardiac surgery", in: Anesth Analg 1986, vol. 65, p 1013, which is incorporated herein by reference) reported poor correlation between aortic diameters measured intraoperatively to those measured by a commercially available A-mode echo device preoperatively. In addition, errors in echo-cardiographic diameter are magnified in the second power since the area of a circle is a quadratic function of its radius.

Furthermore, the measured anatomic cross-sectional area CSA of the ascending aorta, and the effective cross-sectional area in which the blood is flowing, may not be equivalent (see Ihlen H, Amlie J P, Dale J, et al., "Determination of cardiac output by Doppler echocardiography", in: Br Heart J 1984, vol. 51, p. 54, which is incorporated herein by reference). If laminar flow conditions are operative in the proximal ascending aorta, a zone of zero flow must be present, i.e. a small boundary layer of blood which is not flowing exists between the luminal valve and the blood undergoing acceleration and deceleration.

Errors in the velocity measurement are increased by interrogating the axial blood flow at an angle >0° by the emitted ultrasonic signal. When the suprasternal acoustic window is used, there are conditions where >20° interrogating angles are unavoidable for anatomical and technical reasons. This may lead to larger errors regarding the velocity calculations.

In order to improve the measurement quality, often esophageal Doppler velocimetry is used.

Esophageal Doppler velocimetry, which can realistically be deployed only under anesthesia, has some advantages compared to the Doppler techniques applied to the suprasternal acoustic window:

a) Since the measurement site within the esophagus is closely located to the descending aorta, the ultrasound has closer access to the source of the frequency shift, promoting a better signal-to-noise ratio.

b) The ultrasound transducer is, related to its position, more fixated within the esophagus than a hand-held transducer applied to the suprasternal acoustic window.

However, in esophageal Doppler velocimetry, the aortic valve cross-sectional area also has to be determined by using the same assumptions, which cause the problems cited above.

Commercially available esophageal Doppler velocimeters estimate the aortic valve cross-sectional area via M-mode Doppler measurements, or, more simplified, by regression equations incorporating anthropometric measurements, like those published by Henry et al. (see Henry W L, Gardin J M, Ware J H, "Echocardiographic measurements in normal subjects from infancy to old age", in: Circulation 1980, vol. 62, 5, p.1054–1061, which is incorporated herein by reference).

In the prior art, both in Doppler velocimetry applied to the suprasternal acoustic window and in esophageal Doppler velocimetry, there is no unanimity of opinion regarding which echocardiographic method or convention should be employed for the determination of the cross-sectional area of the aorta, and which site or sites are most suitable for the cross-sectional area and velocity analyses. To-date, no method has been found which is so convincing that other approaches have been abandoned. The most crucial point is the determination of the cross-sectional area, which is time-consuming and cumbersome, nevertheless, does not lead to optimal results. Furthermore, its employment is totally user dependent.

SUMMARY OF THE INVENTION

It is an object of the invention to provide a method and an apparatus for monitoring the stroke volume SV of a subject's heart, which can in particular be used during the course of thoracic surgical operations, in which the thorax of the subject is opened and which, at the same time, is more reliable than the prior art methods.

The solution according to the present invention consists in still using Doppler velocimetry, but wherein a calibration process is performed in preparation of Doppler velocimetry measurements rather than determining the cross-sectional area of the aortic valve by a direct measurement.

In a first step of the inventive method, a reference stroke volume $SV_{REF}$ is determined by a first method different from Doppler velocimetry, which is sufficiently reliable and preferably highly reliable. In a preferred embodiment, the first method is based on the measurement of transthoracic electric bioimpedance (or bioadmittance), TEB, using surface electrodes applied to neck and thorax of the subject, or the first method is based on the esophageal electrical bioimpedance or bioadmittance measurement, EEB, where the electrodes are placed on a catheter to be inserted into the esophagus. $SV_{REF}$ can be calculated according to the Kubicek or Sramek patents incorporated by reference above, but preferably the calculation disclosed in US patent application Ser. No. 09/824,942, which is incorporated herein by reference, is used.

In a second step, a reference systolic velocity integral ($SVI_{CAL}$) is determined by Doppler velocimetry simultaneously with the determination of the reference stroke volume $SV_{REF}$.

In the following, it is assumed that the stroke volume by Doppler Velocimetry ($SV_{DV}$) is proportional to the systolic velocity integral SVI, i.e. equals SVI multiplied by a constant k:

$$SV_{DV} = k \cdot SVI.$$

Since the stroke volume determined by the first, reference, method ($SV_{REF}$) and the reference systolic integral ($SVI_{CAL}$) have been determined at the same time (calibration process), the stroke volume calculated on the basis of the reference systolic velocity integral $SV_{DVCAL}$ must equal the reference stroke volume $SV_{REF}$:

$$SV_{REF} = SV_{DVCAL} = k_{CAL} \cdot SVI_{CAL}.$$

Since the constant $k_{CAL}$ is the only unknown parameter in this equation, it can be determined to $$k_{CAL} = SV_{REF}/SVI_{CAL}.$$

After this calibration process, further Doppler velocimetry measurements can be undertaken without the need of additionally using the reference method different from Doppler velocimetry, as long as the position of the Doppler measurement means has not been changed, and one obtains for the stroke volume at a time after the calibration:

$$SV_{DV} = k_{CAL} \cdot SVI = \frac{SV_{REF}}{SVI_{CAL}} \cdot SVI.$$

In the present invention, it is no longer necessary to estimate the cross-sectional area of the aorta. A further important advantage of the inventive method is that there is no requirement to determine the systolic velocity integral at the site of maximum flow amplitude, or to find the exact incidence between the axial flow of blood and the ultrasonic beam emitted by the Doppler velocimeter means. As long as a significant systolic velocity integral is obtained and the Doppler velocity measurement means is maintained in a fixed position, Doppler velocimetry measurements of stroke volume provide results which are as accurate as those obtained by the reference method used for the calibration.

In a preferred embodiment, esophageal Doppler velocimetry is used wherein a transducer is placed on a catheter which can be inserted into the esophagus of the subject. If the reference method makes use of esophageal electrical bioimpedance measurements (EEB), the electrodes can be placed on the same catheter.

The invention also provides an apparatus for monitoring the stroke volume of a subject's heart at different times comprising a unit for a reference measurement of the stroke volume, such as a thoracic impedance measurement unit, including an alternating current (AC) source and a voltmeter, both being connected to electrodes, or being at least adapted to be connected to these electrodes. The apparatus further comprises a Doppler velocimeter unit including a control means for controlling an ultrasound emitter, and signal receiving means for obtaining signals from an ultrasound receiver. Furthermore, a processing unit is provided, which is connected to said reference unit and said Doppler velocimeter unit such that the constant $k_{CAL}$ can be calculated.

The apparatus described immediately above can be combined with the above-mentioned esophageal catheter such that a system for monitoring the stroke volume is obtained. The stroke volume can be displayed on a display. Furthermore, an interface can be provided in order to input data for the calculation of the stroke volume which is, for example, necessary when the method disclosed in U.S. patent application Ser. No. 09/824,942 incorporated above is used.

The method and the apparatus according to the invention have the advantage that they can be applied in thoracic surgery wherein the reference measurement based on transthoracic or esophageal electrical bioimpedance/bioadmittance measurements is performed while the thorax is integer, i.e. not yet opened, while during surgical intervention Doppler velocimetry is applied, which is then, due to the calibration, as reliable as the bioimpedance/bioadmittance based determination of the stroke volume. The Doppler velocimeter and the electrical bioadmittance/bioimpedance interfaces can be integrated into one device, wherein in the prior art for the determination of the aortic valve cross-sectional area a completely different equipment has to be used.

In the event that, during calibration, the systolic velocity integral is obtained at the site of maximum flow amplitude, and the exact incidence between axial blood flow and emitted ultrasound beam is found, the constant $k_{CAL}$ is equivalent to the aortic cross-sectional area (CSA). Thus, the parallel application of Thoracic Electrical Bioimpedance and Doppler Velocimetry can also be used to determine the aortic cross-sectional area (CSA).

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE DRAWINGS

Figure 1:
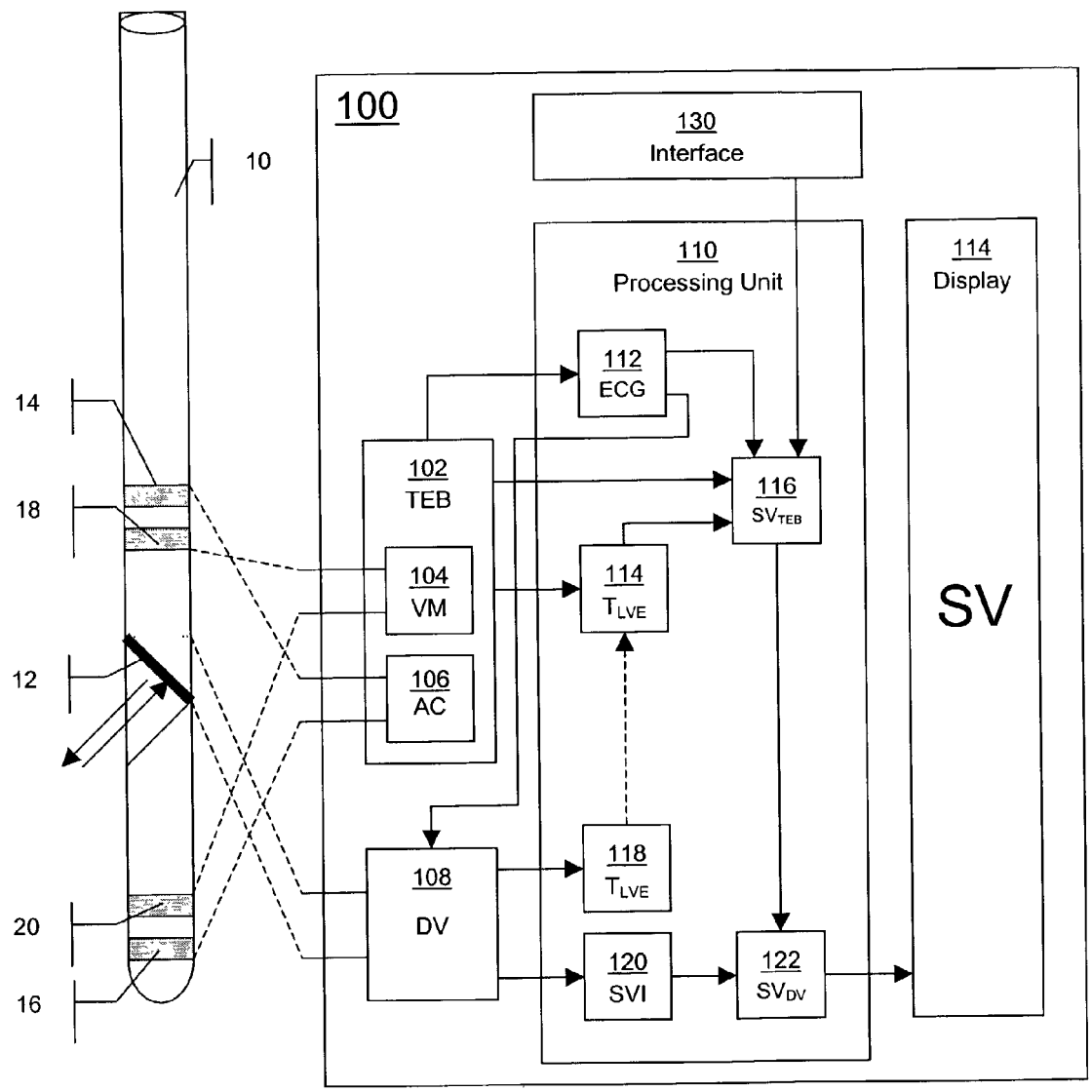
FIG. 1 shows a block diagram of an apparatus according to one embodiment of the present invention together with a schematically shown catheter, which can be used together with this apparatus

FIG. 1 illustrates a portion of an esophageal catheter/probe 10 and the system. An ultrasound crystal 12 is mounted at a specific angle on the body of the catheter 10. The angle is determined empirically in order to obtain best inclination to axial blood flow in the descending thoracic aorta. Ultrasound crystal 12 is connected to a Doppler velocimeter 108, which is integrated into an apparatus 100 according to the present invention. According to FIG. 1, a single ultrasound crystal 12 is utilized for emission of the generated ultrasound signal and detection of the reflected ultrasound signal. Alternatively, separately crystals can be used for emission and detection of ultrasound signals (not shown).

In order to be able to provide a calibration for the stroke volume determination on the basis of Doppler velocimetry, the stroke volume is determined by esophageal electrical bioimpedance measurement. To this end, four ring electrodes 14, 16, 18, 20 are located on the catheter. Outer electrodes 14, 16 are used to apply a low amplitude, high frequency current generated by an alternating current (AC) source 106 being part of a TEB (thoracic electrical bioimpedance) unit 102, which is integrated into apparatus 100. A voltmeter 104 is connected to the two inner electrodes 18, 20 and obtains the voltage drop as a result of the applied current. The connections between apparatus 100 and the esophageal catheter are indicated by dashed lines, because the actual connections are implemented via wires going from the apparatus to the inside lumen of catheter 10. Alternatively, instead of using separate current application and voltage sensing electrodes, the same electrodes can be used for both functions.

In addition to TEB unit 102 and Doppler velocimeter, 108, apparatus 100 incorporated a processing unit 110 and a display 140. Additional interfaces 130 may be optional. Through voltmeter 104, an electrocardiogram ECG can be obtained. Alternatively, the ECG may be obtained by a separate voltmeter. Processing unit 110 comprises an electrocardiogram unit 112, which determines the cardiac cycle length and the heart rate and provides a heart rate synchronous trigger signal to Doppler velocimeter 108. The TEB unit determines from the impedance waveforms the various relevant impedance parameters and the left-ventricular ejection time 114, as described in U.S. patent application Ser. No. 09/824,942 incorporated above. With the additional input of the subject's weight entered via an interface 130, such as a keypad, keyboard, touch screen or data line, stroke volume, obtained by means of thoracic electrical bioimpedance, is calculated in unit 116 and used for calibration of stroke volume, obtained by Doppler velocimetry in unit 122.

Alternatively, or in addition (as indicated by a dashed arrow), the left-ventricular ejection time is obtained from the Doppler velocity profile 118, considering that the systolic velocity integral (SVI) 120 is calculated as the integral under the velocity profile during ventricular ejection time. The ejection time measurements by TEB and Doppler velocimetry may be averaged with a weighting factor depending, for example, on signal quality.

The stroke volume determined by bioimpedance-calibrated Doppler velocimetry is presented on a display 140.

Figure 2:
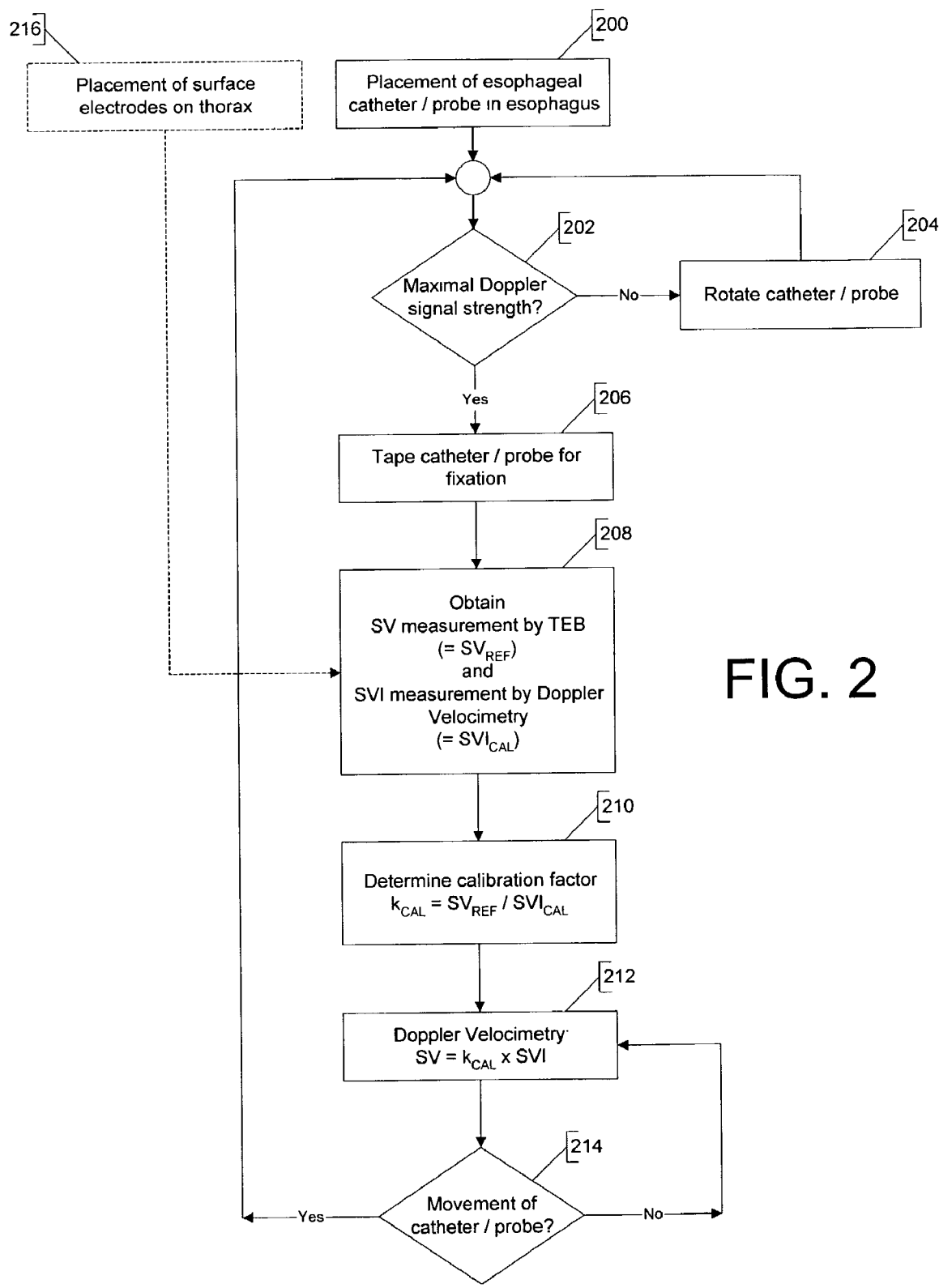
FIG. 2 shows a flow diagram of the method according to the present invention.

FIG. 2 shows a flow diagram illustrating the method of monitoring the stroke volume SV according to the invention in which apparatus 100 and catheter/probe 10 shown in FIG. 1 are used.

First, in step 200, esophageal catheter/probe 10 of FIG. 1 is placed in the esophagus of a patient. The distance how far the catheter is inserted into the esophagus is dictated by the height of the patient.

In a next step, Doppler velocimeter 108 activates transducer 12 of FIG. 1 and receives echo signals therefrom. It is then checked if the Doppler signal strength is maximal. If not, catheter 10 is rotated (step 204) until the maximum Doppler signal strength is reached. If the maximum Doppler signal strength is reached, catheter 10 is fixed in its present position (step 206). This is usually accomplished by taping the catheter to the face of the patient.

Thereafter, the apparatus is initialized. Patient data, such as height, weight, age and gender (which are used for the SV determination), are entered via interface 130. Then, two processes are performed in parallel. One of these processes is the measurement of the stroke volume $SV_{REF}$ by means of thoracic electrical bioimpedance analysis. Simultaneously, Doppler velocimetry is used to measure a systolic velocity integral $SVI_{CAL}$. Both these processes are performed in step 208.

In a next step (step 210), the calibration factor $k_{CAL}$ is determined, $k_{CAL}$ $SV_{REF}/SVI_{CAL}$.

Thence, at the later time period, TEB unit 102 of apparatus 100 of FIG. 1 is disabled, and only Doppler velocimetry by Doppler velocimeter 108 of apparatus 100 of FIG. 1 continues. This is step 212. The Doppler velocimeter records the systolic velocity integral SVI with each cardiac cycle, and processing unit 110 of apparatus 100 of FIG. 1 calculates the stroke volume SV according to the formula $SV = k_{CAL} \cdot SVI$.

Thereafter, it is checked in step 214 if catheter 10 of FIG. 1 has been moved. If not, step 212 is repeated, i.e., the stroke volume SV is determined for still a later point in time (or, more precisely, time interval). If catheter 10 has been moved, the method returns to step 202 in order to repeat the calibration process.

In an alternative version of the inventive method, electrodes placed on the thorax of the patient are used for electrical bioimpedance measurement instead of electrodes 14, 16, 18, 20 placed on the catheter 10 shown in FIG. 1. In this case, steps 200, 202, 204 and 206 still have to be performed in order to optimize the Doppler signal. Prior to step 218, the surface electrodes have to be placed on the thorax (step 216) in a well-known manner. This includes checking the electrode gel interface etc.

As mentioned above, the invention is not limited to the embodiments described with respect to FIG. 1 and 2. In particular, a reference method different from electrical bioimpedance/bioadmittance measurement can be used for the calibration. Furthermore, instead of esophageal Doppler velocimetry, Doppler velocimetry can be applied via the suprasternal acoustic window.

The invention is defined solely by the appended claims and equivalents thereof and therefore includes modifications of the embodiments described above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of monitoring the stroke volume (SV) of a subject's heart at different time periods, comprising the steps of:
   determining a reference stroke volume ($SV_{REF}$) of the subject's heart by a first method different from Doppler velocimetry in a first time period;
   simultaneously determining a reference systolic velocity integral ($SVI_{CAL}$) by Doppler velocimetry;
   calculating a constant $k_{CAL}$, wherein $k_{CAL} = SV_{REF}/SVI_{CAL}$;

determining a systolic velocity integral (SVI) at later time periods by Doppler velocimetry; and
   determining the stroke volume (SV) at said later periods by setting $SV = k_{CAL} \cdot SVL$.

2. The method of claim 1, wherein said first method uses one of the group of transthoracic electrical impedance measurements and transthoracic electrical bioadmittance measurements.

3. The method of claim 1, wherein said first method uses one of the group of esophageal electrical bioimpedance measurements and esophageal electrical bioadmittance measurements.

4. The method of claim 1, wherein esophageal Doppler velocimetry is used.

5. The method of claim 4, wherein, prior to determining said reference stroke volume ($SV_{REF}$) and said reference systolic velocity integral ($SVI_{CAL}$),
   a) a catheter comprising a device for performing Doppler velocimetry by obtaining Doppler signals is inserted into the subject's esophagus,
   b) said catheter is rotated until substantially maximal Doppler signal strength is obtained, and
   c) said catheter is fixed such that it can no longer be rotated.

6. The method of claim 4, wherein a catheter comprising a device for performing Doppler velocimetry is inserted into the subject's esophagus, and wherein it is attempted to hold the catheter fixed starting at least from said determination of said reference stroke volume ($SV_{REF}$) and said reference systolic velocity integral ($SVI_{CAL}$), and
   wherein after each movement of said catheter, despite said attempt to hold the catheter fixed, said reference stroke volume ($SV_{REF}$) and said reference systolic velocity integral ($SVI_{CAL}$) are newly determined and said constant $k_{CAL}$ is newly calculated, and
   wherein said newly calculated $k_{CAL}$ is used for the determination of the stroke volume (SV) until a new movement of said cathete occurs.

7. The method of claim 1, wherein during said Doppler velocimetry, a transducer is applied to the suprasternal acoustic window.

8. A method of monitoring the cardiac output (CO) of a subject's heart, comprising:
   determining the stroke volume (SV) of the subject's heart by using the method according to claim 1;
   determining the heart rate (HR) of the subject's heart; and
   calculating the cardiac output as, $CO = SV \cdot HR$.

9. The method according to claim 8, wherein the heart rate (HR) is determined by using an electrocardiogram.

10. A system for monitoring the stroke volume (SV) of a subject's heart at different times, comprising:
    a reference device for determining a reference stroke volume ($SV_{REF}$) by using a first method different from Doppler velocimetry;
    a Doppler velocimeter for determining reference systolic velocity integral ($SVI_{REF}$) and systolic velocity integral (SVI) at different times; and
    a device for calculating, said calculating device being adapted to obtain the reference stroke volume ($SV_{REF}$) from said reference device and the systolic velocity integral from said velocimeter.

11. A system for monitoring the stroke volume (SV) of a subject's heart at different times, comprising:
    a reference device for determining a reference stroke volume ($SV_{REF}$) by using a first method different from Doppler velocimetry;
    a Doppler velocimeter for determining reference systolic velocity integral ($SVI_{REF}$) and systolic velocity integral (SVI) at different times;
    a device for calculating; and
    a controller for switching between:
    a) a calibration mode in which said reference device and said Doppler velocimeter are activated, and
    b) a measurement mode in which only said Doppler velocimeter is activated.

12. An apparatus for monitoring the stroke volume (SV) of a subject's heart at different times, comprising:
    a thoracic impedance measuring unit, including:
        an alternating current (AC) source connected to two ports for attaching electrodes, and
        a voltmeter connected to two ports for attaching electrodes;
    a Doppler velocimeter unit including a controller for controlling an ultrasound emitter and a signal receiving device for obtaining signals from an ultrasound receiver; and
    a processing unit connected to said thoracic impedance measuring unit and said Doppler velocimeter unit, said processing unit being adapted to obtain a reference stroke volume ($SV_{REF}$) from said thoracic impedance measuring unit and a systolic velocity integral from said velocimeter.

13. The apparatus of claim 12, further comprising an interface for inputting data into said processing unit.

14. The apparatus of claim 12, further comprising a display.

15. A system for monitoring the stroke volume (SV) of a subject's heart, comprising:
   the apparatus of claim 12; and
   a catheter which is adapted to be inserted into the subject's esophagus, wherein an ultrasound transducer is mounted on said catheter, said transducer being electrically connected to said Doppler velocimetry unit of said apparatus.

16. The system of claim 15, wherein four electrodes are mounted in two pairs on said catheter and wherein a first electrode of each pair is electrically connected to said alternating current (AC) source of said apparatus and a second electrode of each pair is electrically connected to said voltmeter of said apparatus, and wherein said second electrodes are located closer to each other than said first electrodes.

17. The apparatus of claim 12, further comprising a device adapted to be inserted into a subject's esophagus, said device comprising:
   a catheter,
   at least two electrodes on the catheter; and
   an ultrasound emitter and ultrasound receiver for Doppler velocimetry on the catheter.

18. The apparatus of claim 17, wherein said transducer is placed in the center of the electrodes.

19. The apparatus of claim 18, wherein four electrodes are mounted on the catheter in a pairwise arrangement, one of said pairs being placed nearer to the transducer than the other pair.

* * * * *

UNITED STATES PATENT AND TRADEMARK OFFICE
CERTIFICATE OF CORRECTION

PATENT NO.        : 7,186,219 B2
APPLICATION NO.   : 10/268120
DATED             : March 6, 2007
INVENTOR(S)       : Markus J. Osypka et al.

It is certified that error appears in the above-identified patent and that said Letters Patent is hereby corrected as shown below:

On The Title Page Item -56- References Cited:
Other Publications, line 2: change "anestheslotogy" to -- anesthesiology --.

Column 9, Line 38:
Change "$SV=k_{CAL} \cdot SVL$" to -- $SV=k_{CAL} \cdot SVI$ --.

Column 10, Line 6:
Change "cathete" to -- catheter --.

Signed and Sealed this

Twenty-ninth Day of May, 2007

JON W. DUDAS
*Director of the United States Patent and Trademark Office*